United States Patent [19]

Discko, Jr.

[11] Patent Number: 5,129,825
[45] Date of Patent: Jul. 14, 1992

[54] DENTAL SYRINGE AND CAPSULE FOR USE THEREWITH

[76] Inventor: John Discko, Jr., 50 Laura Rd., Hamden, Conn. 06514

[21] Appl. No.: 418,585

[22] Filed: Oct. 10, 1989

Related U.S. Application Data

[63] Continuation-in-part of Ser. No. 136,200, Dec. 21, 1987, abandoned.

[51] Int. Cl.$^5$ .............................................. A61C 5/04
[52] U.S. Cl. .................... 433/90; 239/587.1; 222/325; 604/232
[58] Field of Search ............... 433/90; 604/403, 232, 604/72, 218, 225, 228, 239, 207, 125, 275; 222/325, 326, 567, 340, 341, 336; 239/587

[56] References Cited

U.S. PATENT DOCUMENTS

| | | | |
|---|---|---|---|
| 3,724,077 | 4/1973 | Preston et al. | 433/90 |
| 3,900,954 | 8/1975 | Dragan | 433/90 |
| 4,384,853 | 5/1983 | Welsh | 433/90 |
| 4,457,712 | 7/1984 | Dragan | 433/90 |
| 4,758,158 | 7/1988 | Pierce et al. | 433/90 |
| 4,767,326 | 8/1988 | Bennett et al. | 433/90 |
| 4,931,040 | 6/1990 | Haber et al. | 604/232 |

FOREIGN PATENT DOCUMENTS

| | | | |
|---|---|---|---|
| 0077150 | 4/1983 | European Pat. Off. | 433/229 |
| 0237182 | 9/1987 | European Pat. Off. | 433/90 |

Primary Examiner—Cary E. Stone
Assistant Examiner—Adriene B. Lepiane
Attorney, Agent, or Firm—Arthur T. Fattibene; Paul A. Fattibene

[57] ABSTRACT

This disclosure is directed to a dental syringe having a capsule holder and a plunger for accurately and precisely placing a viscous or low viscosity composite resin dental restorative material from a capsule directly into a tooth. The improvement resides in a plunger having an ejector tip which is maintained under a positive bias that is intended to retract when a resistance exceeding a predetermined amount is met during an ejecting procedure so as to prevent any build-up of pressure within the capsule containing the material to be dispensed that may tend to distort or rupture the capsule. In the case of a low viscosity resin, the plunger having an ejector tip maintained under a positive bias that is intended to retract when the speed of ejection exceeds that of a predetermined rate, so as to prevent sudden and excessive extrusion of material from the capsule. The capsule containing the viscous material may also be provided with a reinforced body portion to further aid in resisting any built-up internal pressure within the capsule during an ejecting procedure. The capsule may also include orientation notches formed on the flange for engaging a stop detent for positively maintaining the capsule in a predetermined oriented angular position relative to the holder.

4 Claims, 2 Drawing Sheets

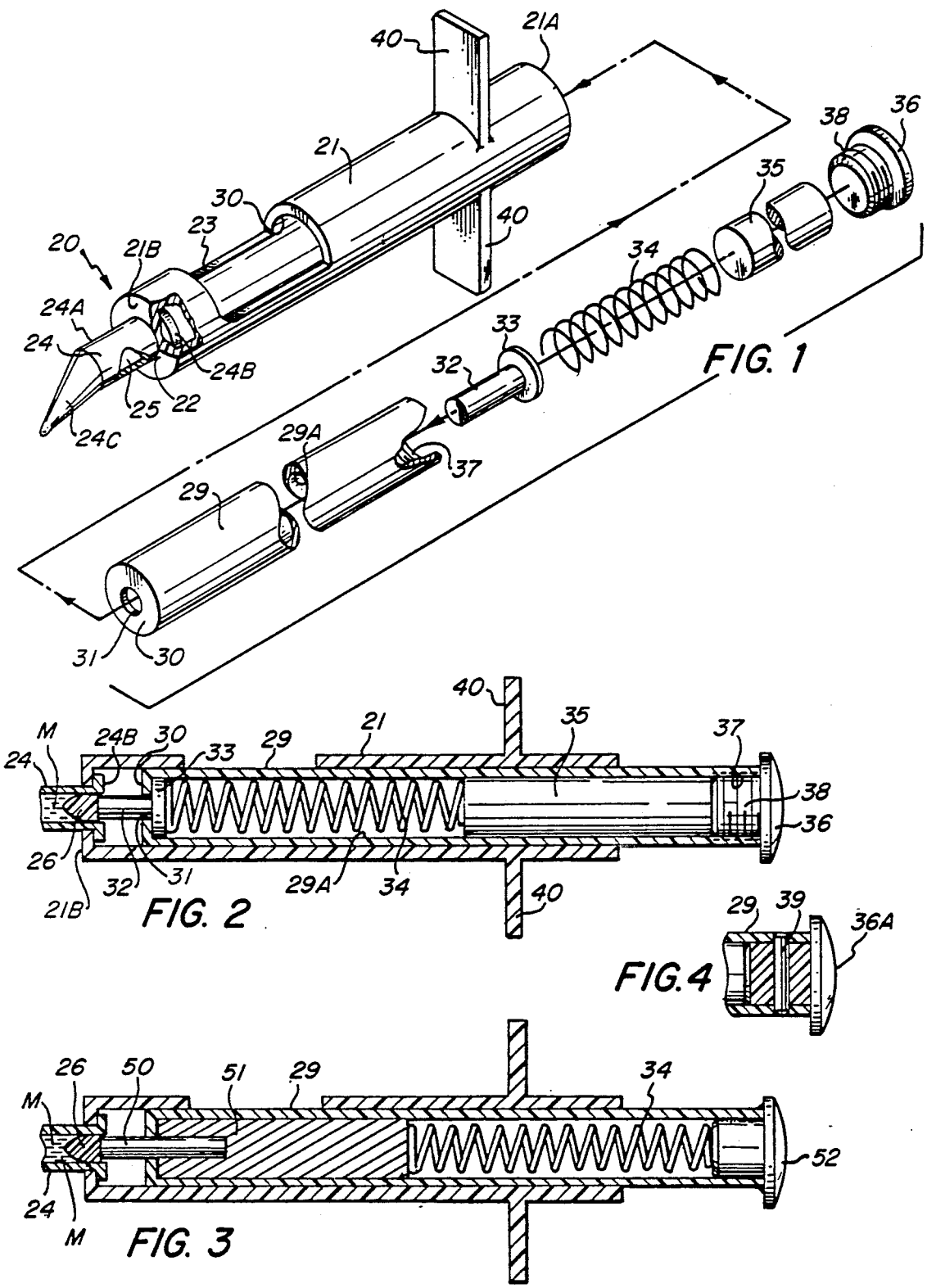

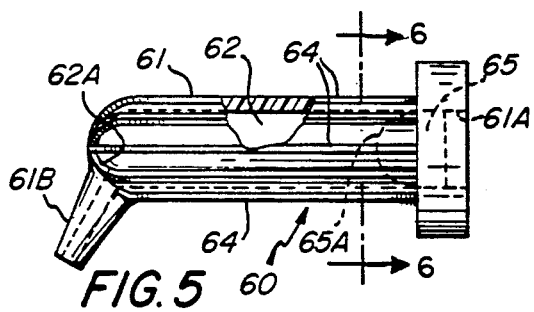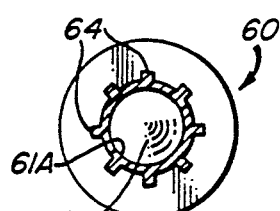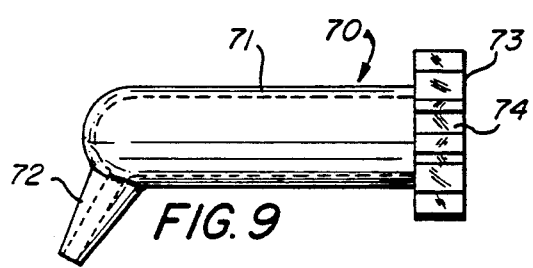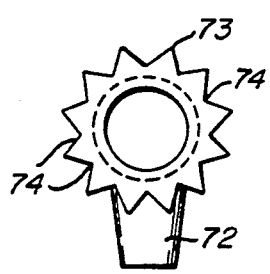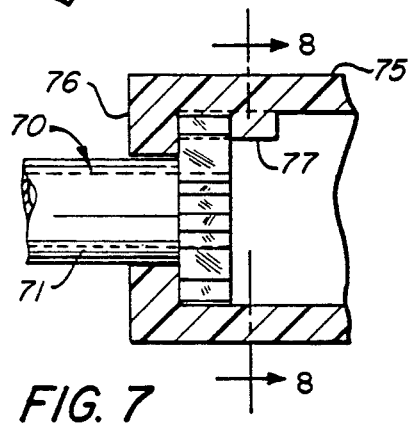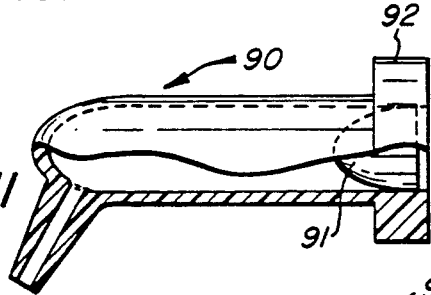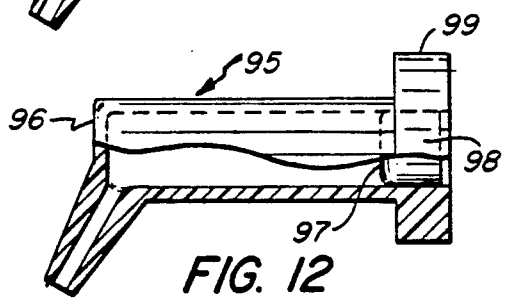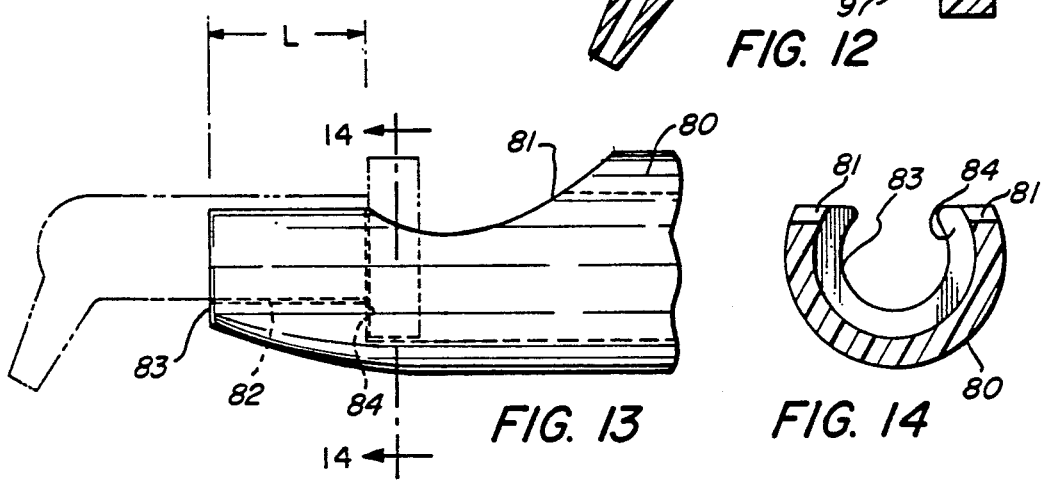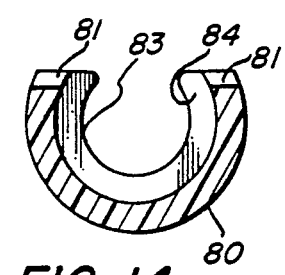

DENTAL SYRINGE AND CAPSULE FOR USE THEREWITH

RELATED APPLICATIONS

This is a continuation in part application of application Ser. No. 07/136,200 filed Dec. 21, 1987 and abandoned for Dental Syringe and Capsule for Use Therewith.

This invention relates generally to a dental placement syringe and capsule for use therewith, for use by a dentist to effect the direct placement of a composite resin material or other dental material from the syringe directly to a tooth.

PROBLEM AND PRIOR ART

With the advent of the ever increasing use by dentists of composite resin material for tooth restorations came the discovery of the syringing technique for effecting the direct placement of composite dental restorative material to a tooth as disclosed in U.S. Pat. No. 3,581,399 granted Jun. 1, 1971. Subsequently, other syringe constructions for the direct placement of composite resin materials were made as disclosed in the other prior patents, viz. U.S. Pat. Nos. 3,900,954 and 4,198,756. These various syringe devices invented by Dr. William B. Dragan comprised in general a syringe holder having a tubular barrel having a plunger and a readily disposable capsule detachably connected to the end of the barrel for containing the dental material to be dispensed. Such capsules or cartridges were either loaded by the dentist with his composite material of choice, or factory loaded with a given composite material by or for a specific material manufacturer. With the success of the syringing technique, others sought to enter the marketplace as evidenced by the granting of U.S. Pat. Nos. 4,295,828; 4,391,590; 4,384,853 and 4,330,280, which embody essentially the same general concept or theme for effecting the syringe technique described in my U.S. Pat. No. 3,581,399. In each of the foregoing noted syringe constructions, the viscous dental material was loaded into a capsule which was made of a suitable plastic material; and the material thereafter extruded from the capsule by the exertion of a plunger force on the piston closing the end of the capsule. Because of the increasing viscosity of the composite resin dental material, which varied from manufacturer to manufacturer, and the relatively small discharge orifice through which the material was required to be extruded, the walls of the capsule are subjected to tremendous pressure during an extruding operation. For this reason, the dentist, upon the purchase of such syringes, is instructed to use a slow, steady pressure on the plunger of the syringe so as to control or prevent any excessive build-up of pressure from occurring within the capsule. However, despite such instruction, it has been noted that many dentists would disregard such instructions and would attempt to extrude the material quickly and/or apply excessive force on the plunger of the syringe during an extruding operation. When this occurred, the walls of the capsule may tend to bulge, distort or rupture. Thus, unless the dentist followed the manufacturer's instructions of exerting only a slow steady pressure on the plunger of the syringe, the walls of the capsule could distort. This defect could deter a dentist from using a syringe. Thus, the advantage of the syringing technique may not be fully appreciated by a dentist; and/or discouraged some dentists from using the syringe technique for placing the composite. The syringe technique has been acknowledged as the more accepted procedure for placing composites, as air voids are reduced to a minimum by syringing, in addition to other acknowledged advantages such as less waste, convenience and efficiency. The foregoing noted problem has been further aggravated by the composite material manufacturer's desire to render such composite material more packable by increasing the filler content thereof, and thereby making the material extremely viscous. Efforts to syringe such high viscous material subjected the walls of the capsule to even greater pressure. In the case of a low viscosity material, whereby high extrusion forces are not necessary and are contraindicated, control of easily flowable materials in small quantities becomes difficult because in such instance, only very minute movements of the hand or little pressure is required. Often, to overcome the initial friction and resistance, an operator would tend to squeeze the syringe device too abruptly, and thus, with too much force, resulting in extruding an excessive amount of such low viscosity materials.

Also, in the syringe constructions of the foregoing cited prior art, it was possible to rotate the dispensing tip or nozzle of the capsule about a 360° rotation relative to the syringe barrel, but contained no means for positively maintaining the capsule in a desired position.

In each of the prior art structures, the selected position of the capsule was maintained simply by the snugness of the fit between the capsule and the barrel end of the syringe holder. Frequently, due to wear and/or variance in manufacturing tolerances, the desired orientation of the capsule could not be positively maintained by friction alone.

Another problem that has been observed is that due to the fear of AIDS and other contagious diseases, more and more dentists are using rubber gloves in their practice. It has been noted that in working with rubber gloves, considerable difficulty is encountered in handling certain dental tools and appliances, and in particular the handling of small capsules used for the placement of composite materials that are required to be loaded into a syringe ejector. This is because the capsules, being quite small and smooth, render the handling difficult with rubber gloves, since the amount of feeling one can achieve with rubber gloves is greatly limited.

OBJECTS

An object of this invention is to provide in a dental composite resin placement syringe, a plunger construction that prohibits any excessive build-up of pressure within the capsule regardless of how forceful a dentist may operate the syringe and/or how viscous the material.

Another object is to provide a dental syringe for effecting the placement of high or low viscosity composite resin material with a plunger arrangement which is capable of applying the requisite amount of extruding force on the material contained within the capsule while automatically prohibiting the application of any excessive force that may result in rupturing of the capsule or in the case of a low viscosity resin, applying too much force and extruding an excessive amount.

Another object is to provide an improved capsule construction for resisting any built-up internal forces which may cause rupturing of the capsule in the event an excessive amount of force is inadvertantly applied thereto.

Another object is to provide an improved capsule construction arranged to be angularly orientated and positively secured in its desired orientated position.

Another object is to provide a capsule constructed so as to facilitate the handling thereof, and particularly when a dentist is wearing rubber gloves.

SUMMARY OF THE INVENTION

The foregoing objects and other features and advantages of this invention are attained by a dental syringe for effecting the placement of a composite resin dental material directly into a tooth cavity which includes a holder comprising an elongated barrel having an end portion provided with a longitudinally extending slot and an adjacent front opening for detachably receiving a capsule or cartridge containing a predetermined amount of the composite resin material to be dispensed therefrom. The elongated barrel may be provided adjacent the other end thereof with a finger grip, such as is disclosed in U.S. Pat. No. 3,581,399, or a lever actuator arranged to operate on the plunger as first disclosed in U.S. Pat. No. 4,198,756 and as shown and adapted in later issued patents, e.g., U.S. Pat. Nos. 4,295,828; 4,384,853 and 4,330,280.

Capsules for use with such dental syringes comprise a plastic cartridge having a body portion provided with an open end portion at one end and having a discharging nozzle tip portion connected to the other end thereof. Generally, the capsule is sized to accommodate a predetermined amount of composite resin material sufficient to provide a unit dose, and is sealed within the capsule by a displaceable end plug or piston. Such typical capsules are disclosed in the above noted cited prior patents. Such capsules are formed of an all plastic material, e.g. polypropelyne, nylon, Zytel nylon and the like. Because of the nature of the material and the construction of the capsule, the thickness of the walls of the chamber containing the viscous dental material could resist only limited pressures before they would tend to bulge or rupture. For this reason, dentists were advised by the manufacturers to use only a slow, steady pressure when operating such syringes. As long as the instructions were followed, satisfactory operation was effected. However, because instructions were not always followed, some dentists would actuate the plunger too rapidly and/or with excess force. When this occurred, the compression of the viscous material within the capsule would exert tremendous forces on the walls of the capsule which could result in a rupture. In the case of low viscosity materials, the over compression would result in an excess of material being ejected through the nozzle. To obviate such problems, the present invention contemplates a plunger construction and a capsule construction to resist and/or prevent such excessive built-up forces within the capsule during an extruding operation. In one form of the invention, this is attained by a plunger construction which includes an ejector tip which engages the piston of the capsules to be resiliently loaded, e.g., by a spring, and which is arranged to retract against the bias imposed thereon so as to prevent any excessive build-up of pressure within the capsule or to moderate the extrusion force applied by the operator. In the case of high viscosity materials, the arrangement is such that resistance or bias exerted by the spring is slightly less than the force at which the walls of the capsule would rupture, so that when the wall rupture pressure is approached, the ejector is retracted to prohibit the wall rupturing pressure from occurring. For low viscosity materials, the spring bias is much less, and designed to prevent over pressure from being applied to the capsule.

In another form of the invention, the capsule is constructed with circumferentially spaced reinforcing ribs to strengthen the walls of the capsules. Also, the flange of the capsule may be provided with locating notches adapted to secure the capsule in a desired predetermined oriented position.

FEATURES

A feature of this invention resides in an improved plunger construction for use in a composite resin placement syringe having a resiliently biased displaceable ejector tip to prohibit any excessive build up of pressure within a capsule during an extruding operation, or of excessive pressure extruding a sudden, uncontrollable quantity of material.

Another feature of this invention resides in the provision of a dental syringe of the type having a capsule containing a dental material and a plunger wherein the plunger is provided with a displaceable ejector tip which is maintained under a bias or force which is slightly less than the force required to rupture or distort the capsule wall, or to prohibit any sudden, excessive flow of material.

Another feature of this invention is to provide an improved capsule construction for resisting the rupturing or distortion forces imparted thereto.

Another feature resides in the provision of a capsule construction for dispensing dental material having reinforcing ribs formed along the wall portions thereof.

Another feature is to provide a dental material capsule with a lateral flange having a series of locating notches circumferentially spaced about the periphery thereof.

Another feature resides in providing the exterior surface of the capsule with raised surfaces to facilitate the gripping thereof; and in particular when one is handling the capsule with rubber or protective gloves.

Other features and advantages will become more readily apparent when considered in view of the drawings and specifications in which:

FIG. 1 is a perspective exploded view illustrating a dental syringe embodying the present invention.

FIG. 2 is an assembly view of the syringe construction of FIG. 1 shown in section.

FIG. 3 is a sectional assembly view of a modified syringe construction of this invention.

FIG. 4 is a modified detail of construction.

FIG. 5 is a side view of an improved capsule construction of this invention.

FIG. 6 is a sectional view taken along line 6—6 on FIG. 5.

FIG. 7 is another modified detail of construction.

FIG. 8 is a sectional view taken on line 8—8 of FIG. 7.

FIG. 9 is a modified capsule construction.

FIG. 10 is an end view of FIG. 9.

FIG. 11 is a side view of a modified capsule construction having portions broken away.

FIG. 12 is another modified side view of a capsule construction having parts broken away.

FIG. 13 is a modified detail of construction of a syringe barrel.

FIG. 14 is a sectional view taken on line 14—14 of FIG. 13.

DETAILED DESCRIPTION

Referring to the drawings, there are shown several embodiments of a dental syringe construction embodying the present invention. FIG. 1 illustrates a dental syringe 20, illustrated in an exploded view to illustrate the respective component parts. The illustrated dental syringe 20 of FIG. 1 relates to dental syringes of the type disclosed in prior U.S. Pat. Nos. 3,581,399 and 3,900,954. As it will be apparent, the subject matter of the present invention can also be utilized in a dental syringe construction having a lever or pistol grip type actuator as disclosed in U.S. Pat. No. 4,198,756, and those syringe devices that followed the teachings of the U.S. Pat. No. 4,198,756 such as disclosed in U.S. Pat. Nos. 4,295,828; 4,330,280 and 4,384,853.

The dental syringe 20 comprises a tubular barrel 21 which is open at one end 21A and which is provided with an inturned flange 21B at the other end thereof in which there is defined a front opening 22. Adjacent the front opening 22, the barrel is provided with a side opening 23 to facilitate the insertion of a capsule 24 through the front opening. The capsule 24, as will be hereinafter described, comprises a tubular body portion 24A defining a generally cylindrical internal reservoir chamber 25 for containing a predetermined amount of composite resin dental filling material M. Circumscribing the open end of the reservoir chamber 25 is a laterally extending flange 24B which is adapted to abutt against the inturned flange 21B. Connected in communication with the reservoir chamber is a dispensing tip or nozzle 24C through which the material is extruded. If desired, the dispensing tip or nozzle 24C may be angularly disposed as shown. It will also be understood that the capsule may be formed of a light opaque material and/or color that will resist the passage of ambient light therethrough so as to facilitate the handling, storing and dispensing of light activated composite resin material currently being used by dentists. Capsules of the type described are disclosed in U.S. Patents issued to Dr. Dragan, herein referred to, and in U.S. Pat. No. 4,391,590. As described and shown in said patents, an end plug or piston 26 is fitted into the open end of the capsule 24 to seal the material M therein, and by effecting the displacement of the plug or piston 26, the material can be readily extruded through the dispensing tip or nozzle 24C.

Because the composite resin used for restorative procedures comprises a very viscous material, and may be characterized as being a somewhat solid fluid, the force of extrusion imparted on the piston or plug 26 to effect the extrusion of the material frequently causes the internal pressure within the capsule 24 to become so great as to distort or rupture the walls of the capsule 24. Such phenomenon would occur whenever a rapid or excess force is imparted by the dentist on the plunger of the syringe construction which in turn is transmitted onto the plug 26 of the capsule. While the capsules disclosed in the patents herein cited could satisfactorily withstand the internal pressures when the syringe was operated as instructed with a slow and steady pressure, frequently such instructions were not followed, causing the problem which the present invention obviates. Also, the material manufacturers' desire to increase the viscosity of the composite resin material, particularly for use in posterior teeth, has further aggravated the problem of distortion and/or rupture of the capsule walls. Conversely, with low viscosity dental materials such as sealants, acid gel and the like, the common problem in syringing such material is that there is a tendency to apply too much force or pressure on the plunger of a syringe device, thereby causing an excessive amount of such material to be ejected. To overcome these problems, the following construction is noted.

As shown in FIG. 1, an improved plunger construction 21 is shown for use with the barrel 21 of a syringe or holder 20. The plunger construction of this invention comprises a generally hollow plunger shaft 29 which is reciprocally mounted within the bore 30 of the barrel 21 for movement between a retracted and protracted position. The shaft 29 is provided with a front wall 30A having an aperture 31 formed therein for receiving an ejector or tip 32. The ejector includes a projecting tip portion adapted to engage the piston or plug 26 of the capsule during an extruding operation. Connected to the inner end of the ejector is a flange or collar 33 sized to be received within the bore 29A of the shaft 29. Thus, the collar 33 maintains the alignment of the ejector 32 and prevents the ejector from becoming separated from the plunger shaft 29. Disposed in engagement with the ejector 32 is a compression spring 34 for imparting a bias on the ejector of a predetermined force. For viscous resins or materials, a spring 34 having an approximate 30-pound resistance has been found to be satisfactory in this application. If necessary, a spacer rod 35 may be interposed between the spring 34 and an end cap 36 which closes the end of the plunger shaft 29. The spacer rod 35 is of a sufficient length so as to maintain the spring 34 against the collar 33 of the ejector so that the ejector 32 is maintained in a normally projected position as seen in FIG. 1. In the form of FIG. 1, the plunger shaft 29 is provided with internal threads as at 37 to which the complementary threads 38 on the end cap 36 can be mated to secure the plunger assembly as described. It will be understood that the end cap 36 can be fixed to the plunger shaft by other means. FIG. 4 illustrates a modified construction whereby the end ca 36A is secured to the plunger shaft 29 by means of a lock pin 39 which extends through aligned openings formed in the plunger shaft and the end cap 36A. In another embodiment, the end cap may be fused, welded or otherwise secured to the plunger shaft 29.

It will be understood that the bias or resistance imparted by the spring 34 on the ejector tip 32 is such that when the ejector encounters a resistance which is greater than the spring resistance, the ejector will retract into the plunger shaft. In this manner, a dentist cannot transmit to the piston or plug 26 a pressure or force which is greater than that which the spring imparts on the ejector tip 32. By the selection of a spring 34 having a resistance which is slightly less than the force required to rupture or distort the walls of the capsule, the problem of capsule wall rupture or distortion is completely obviated.

Completing the syringe holder construction, the tubular barrel 21 may be provided with a laterally extending finger grip 40.

While the illustrated embodiment of FIGS. 1 and 2 has a front opening circumscribed by 360° of the barrel, it will be understood that a portion of the tip end of the barrel may be cut away so as to extend the breech opening 23 to the tip end of the barrel to provide a snap-fit retaining means as disclosed in a Brazilian Publication or Utility Model Application No. MU5701465 published Jul. 3, 1979 and/or as subsequently disclosed in U.S. Pat. Nos. 4,330,280 and 4,384,853; all as shown in the cut-away view of U.S. Pat. No. 4,158,756.

FIG. 3 illustrates a modified embodiment of the invention. In this form of the invention, the ejector tip 50 comprises a pin which is secured to a spacer or aligning means 51 slidably disposed within the plunger shaft 29. The compression syringe 34 in turn is disposed between the spacer 51 and the end cap 52. In this embodiment, the end cap 52 may be either fused or bonded to the plunger shaft 29, as shown, or threaded or pinned thereto as described with respect to FIGS. 2 or 4 respectively. In all other respects, the operation of the construction of FIG. 3 is similar to that described with respect to FIGS. 1 and 2.

While the plunger construction described is illustrated for use with a thumb actuated syringe construction as shown in FIGS. 1 to 3, it will be understood that the plunger construction 29 can also be substituted for the plunger used with the lever actuated dental syringe of the type first disclosed in U.S. Pat. No. 4,198,756, and later followed and disclosed in U.S. Pat. Nos. 4,295,828; 4,330,280 and 4,384,853.

The distortion and/or rupturing of capsule carriers of viscous composite resin materials can be further aided by a modified capsule construction. FIGS. 5 and 6 illustrate an improved capsule construction to alleviate the noted problem. As shown in FIGS. 5 and 6, the improved capsule construction 60 comprises an all plastic molded member which comprises a generally cylindrical body portion 61 defining a reservoir chamber 62 adapted to contain a predetermined amount of composite resin material. The internal wall of the chamber 62 is generally cylindrical and open at one end 61A. The other end of the chamber communicates with a discharge nozzle or tip 61B which is preferably angularly disposed to the longitudinal axis of the reservoir chamber 62. In accordance with this invention, the external surface of the body portion 61 is provided with a series of spaced apart longitudinally extending ribs 64 to reinforce the chamber walls of the reservoir chamber 62. The open end of the chamber 62 is closed or sealed by a displaceable end plug 65 as shown. It will be understood that the end plug 65 is provided with an end face 65A which complements the inner wall 62A of the reservoir chamber 62 so as to insure optimum evacuation of all the material contained in the reservoir 62. Thus, the end wall 65A of the end plug 65 and the complementing end wall 62A of chamber 62 may be of any complementary shape, e.g., conical, curvilinear or rectilinear. The material of the capsule may be light resistant for use with light activated materials; and/or may be formed of various colored plastic materials. The longitudinally extending ribs extending along the body portion of the capsule serve to reinforce the body or chamber walls against possible excessive build-up of internal pressures so as to resist any distortion and/or rupture thereof. When the capsules 60 are preloaded by the manufacturer, it will be understood that the orifice opening of the discharge tip 61B may be suitably sealed to protect the material confined therein. Such sealing means may comprise an end sealing cap, plug, cover or any other suitable type of sealing means. It will be further understood that capsule improvements herein described may be applied to variously shaped capsules as will be apparent to one skilled in the art.

The longitudinally extending ribs 64 defining the raised surfaces, in addition to reinforcing the walls of the capsules, also provide a "feel" or grip whereby a dentist can more readily pick up and handle the capsule when wearing rubber gloves. The raised surface area, while shown as ribs, may comprise other suitable shapes which will strengthen the walls of the capsules and provide the "feel" necessary to effect the handling thereof when wearing rubber gloves.

FIGS. 7, 8, 9 and 10 are directed to another feature of the inventions disclosed herein. Referring to FIGS. 9 and 10, there is shown a capsule 70 of a type for use with a placement syringe of the type herein described. The capsule comprises a body portion 71 forming a reservoir for containing the dental material and a discharging tip 72 as hereinbefore described. In this form of the invention, the lateral flange 73 is provided with a series of circumscribing laterally extending ratchet type notches or grooves 74. As will be noted in FIGS. 7 and 8, the front end of the syringe barrel 75 adjacent the inturned front flange 76 is provided with a projecting stop or detent 77 which is adapted to engage one of the notches 74 of capsule 71. When a syringe barrel is provided with a stop detent 77 as shown in FIGS. 7 and 8 and is utilized in conjunction with a capsule such as described with respect to FIGS. 9 and 10, it will be noted that the engagement of the stop 77 with one of the flange notches 74 will serve to positively secure the capsule 71 relative to the barrel 75 of the syringe in a predetermined set angular position. The arrangement is such that the dentist can readily rotate the capsule to a desired angular position, and which position is positively maintained by the inter-engagement of the stop or detent 77 and the notch 74 of the capsule.

In the arrangement described with respect to FIGS. 7 and 8, the angular adjustment of the capsule 70 relative to the syringe barrel 75 is attained by either pushing the capsules inwardly, as seen in FIG. 7 to disengage the notch 74 from the detent 77, rotate the capsule to a desired angular setting and resetting the capsules forwardly to re-engage the detent 77 in the appropriate notch; or the notches 74 can be formed relative to the detent whereby rotation of the capsule causes the notches to merely ratchet relative to the detent in determining the desired angular adjustment.

FIGS. 13 and 14 illustrate a modified barrel construction whereby any of the capsule constructions can be frictionally retained to the end of a barrel with a snap-fit, which is attained by cutting a section or segment of the barrel tip as shown. In the embodiment of FIG. 13, the tubular barrel 80 of the syringe is provided with a side opening 81 immediately adjacent the inturned flange 82 which defines the front opening 83. In this form of the invention, the inturned flange 82 is provided with a length sufficient to engage a portion of the capsule body to maintain the lateral retention of the capsule to the syringe barrel. The relative length L of the inturned flange and the body portion of the capsule is not critical. All that is required is that ratio or L be sufficient to satisfactorily frictionally retain the capsule in the syringe barrel 80. By extending the side opening 81 to the front end 83 of the syringe barrel, the capsule can be readily attached as shown. The inturned flange 82 thus defines a shoulder 84 to engage the lateral flange of the capsule to prevent any axial dislodgement of the capsule during an extruding operation. With the construction described, the side opening 81, as seen in FIG. 14, is sufficiently wide so as to accommodate the width of the capsule flange as the body portion is snap-fitted to the front end of the barrel 80.

The modified barrel construction as described with respect to FIG. 13 comprises a decided improvement, in that the snap-fit of the capsule to the barrel is provided at the top portion of the barrel which facilitates the positioning of the capsule in the end of the barrel and that the extended end of the barrel below the extended opening provides further support for the capsule. Thus, the capsule is not suspended from its ejector holder in accordance with the prior existing art constructions. It will be noted that with the construction described with respect to FIG. 13, there would be no tendency of the capsule to separate from the end of the barrel if for some reason the tolerance between the capsule and the front end of the barrel are insufficient to provide the requisite snap fit retention force. This construction is therefore particularly critical so as to protect or prevent a capsule from dropping out of its ejector holder, particularly when placed in a patient's mouth. Because more and more manufacturers are pre-loading their respective composite resin restorative materials in capsules, and as such capsules may vary in tolerances, it is important for the dentist that regardless of which capsule product he is using, that such capsule product will be properly supported in the end of the ejector holder he is using. Thus, by locating the open end of the retaining slot at the top of the barrel as shown in FIG. 13, rather than at the bottom of the barrel, e.g., as shown in U.S. Pat. Nos. 4,330,280 and 4,384,853 further security is given to both the dentist and the patient that the capsule will not fall out of its ejector holder due to gravity. With the construction shown in FIG. 13, it will be understood that any of the capsule constructions described herein can be utilized therewith. Accordingly, a further advantage is that the barrel construction of FIG. 13 is universally adapted to receive any of the conventionally known capsules as indicated in the noted prior art as well as the improved capsule construction herein described. Also, with the barrel construction described with respect to FIG. 13, it will be noted that the internal bore of the barrel for receiving the plunger 29 terminates directly at the shoulder 84. While the retention of the capsule is attained by the snap-fit of the front end or inturned flange 82 acting on the body of the capsule as indicated at "L", as seen in FIG. 13, additional retention can be attained by dimensioning the flange of the capsule so as to be slightly greater than the internal diameter of the bore of the barrel 80 so that in snap-fitting the body portion of the capsule to the front end of the barrel as shown in FIG. 13, a slightly enlarged flange or collar of the capsule can be simultaneously press fitted to the internal bore of the barrel.

FIG. 11 illustrates a modified capsule construction 90 in which the inner end wall of the capsule is generally eliptical in shape to complement an eliptical shaped piston or plug 91. In FIG. 12, the capsule 95 is provided with a rectilinear or angular end wall 96 to complement a similar shaped end wall 97 of a piston or plug 98. It will be understood that the capsules of FIGS. 11 and 12 may be provided with reinforcing ribs as described with respect to FIGS. 5 and 6. Also, the flange 92 and 99 of FIGS. 11 and 12 may be formed with notches similar to that described with respect to FIGS. 9 and 10.

With low viscosity dental materials such as sealants, acid gel and the like, the plunger spring is selected with a bias that will prevent a dentist from applying too much force on the capsule plug, and thereby avoid any sudden or uncontrolled discharge of the low viscosity material. In such case, only a light syringe is required. Such syringe should have a bias which is only slightly greater than the initial frictional resistance encountered to effect the displacement of the plug within the capsule. In this manner, a more controlled ejection of light or low viscosity material is effected.

From the foregoing, it will be apparent that constructions herein disclosed preclude a dentist from applying such force or pressure on the capsule during an extruding operation that will distort or rupture a capsule. The present invention further provides means whereby the chamber walls of the capsule can be reinforced in a simple and expedient manner and whereby the capsule can be adjusted and positively secured in the adjusted position. Also, a more effective control can be achieved in the ejecting of light or low viscosity dental materials.

While the invention has been described with respect to several embodiments thereof, it will be appreciated and understood that variations and modifications may be made without departing from the spirit or scope of the invention.

What is claimed is:

1. A storage and dispensing capsule for viscous dental materials comprising an elongated unitary tubular body portion defining a reservoir adapted to contain a predetermined amount of dental material, said body portion having a generally cylindrical interior chamber which is open at one end, a discharge nozzle disposed in communication with said interior chamber, said discharge nozzle being disposed at an angle relative to the longitudinal axis of said reservoir, a laterally circumscribing flange disposed about said open end, and said body portion having a series of circumferentially spaced longitudinally extending ribs to resist any internal build-up of pressure that may be developed during the extrusion of the material from said capsule, said ribs being integrally formed of the material of said body portion, and a free plug displaceably disposed within said body portion for extruding the dental material therefrom when displaced, said plug having an end face complementary in shape to the shape of an internal end wall of said body portion.

2. In combination a capsule holder and capsule having a laterally extending flange, said capsule holder comprising a tubular barrel, means on the end of said barrel for detachably receiving the said capsule, said means defining an internal shoulder against which said flange is adapted to abut, and a stop detent means formed on the end of said barrel, said capsule having a plastic body defining a substantially cylindrically shaped reservoir chamber adapted to contain a predetermined amount of dental material, said reservoir chamber being fully open at one end, a discharge tip connected to said body and disposed in communication with said reservoir chamber at the other end thereof, a freely displaceable piston disposed in said reservoir chamber for sealing the open end thereof, said flange having a plurality of notches circumferentially spaced about the outer edge thereof, said notches extending transversely of said outer edge; said stop detent being receivable in one of said notches whereby said capsule can be rotatably adjusted and locked in a predetermined rotary relationship relative to the end of said tubular barrel.

3. A storage and dispensing capsule for viscous dental materials from which the dental material can be readily syringed and to facilitate handling by one wearing protective gloves comprising an elongated tubular body defining a reservoir portion adapted to contain a predetermined amount of dental material, said body portion having a generally cylindrical interior chamber defining said reservoir portion, said reservoir portion being open at one end, a discharge nozzle connected to the other end of said reservoir portion and disposed in communication with said interior chamber, a laterally extending flange disposed about said open end, a displaceable piston for sealing said open end, means formed upon the external surface of said body portion to strengthen said body portion to resist any internal build-up of pressure that may be developed during the extrusion of the material and for providing a grip for facilitating the handling of said capsule by one wearing protective gloves wherein said means comprise a plurality of longitudinally extending raised ribs extending about said body portion and circumferentially spaced thereabout, said ribs being integrally formed on said body portion.

4. A storage and dispensing capsule according to claim 3 wherein said discharge nozzle is disposed at an angle relative to the longitudinal axis of said body portion.

* * * * *